(12) United States Patent
Hoth et al.

(10) Patent No.: US 7,669,493 B2
(45) Date of Patent: Mar. 2, 2010

(54) SPINDLE DRIVE AND A PATIENT POSITIONING SYSTEM

(75) Inventors: Tobias Hoth, Pegnitz (DE); Paul Weidner, Pressath (DE)

(73) Assignee: Siemens Aktiengesellschaft, Munich (DE)

( * ) Notice: Subject to any disclaimer, the term of this patent is extended or adjusted under 35 U.S.C. 154(b) by 713 days.

(21) Appl. No.: 11/542,488

(22) Filed: Oct. 3, 2006

(65) Prior Publication Data

US 2007/0137330 A1 Jun. 21, 2007

(30) Foreign Application Priority Data

Oct. 10, 2005 (DE) .................. 10 2005 048 394

(51) Int. Cl.
*F16H 1/20* (2006.01)
*B66F 3/00* (2006.01)
(52) U.S. Cl. .................. 74/89.26; 254/124; 254/126
(58) Field of Classification Search .......... 74/89, 74/89.23, 89.26, 89.32, 89.33, 89.34, 89.37, 74/89.45; 5/611; 254/100, 102, 103, 124, 254/126
See application file for complete search history.

(56) References Cited

U.S. PATENT DOCUMENTS 2,927,473 A * 3/1960 Bentley .................. 74/89.23
5,394,288 A * 2/1995 Nishida et al. .................. 361/31
5,472,065 A * 12/1995 Vergin .................. 185/40 R
6,789,940 B2 * 9/2004 Meyer et al. .................. 378/196
2005/0103138 A1 * 5/2005 Chen et al. .................. 74/89.26

FOREIGN PATENT DOCUMENTS

GB 896914 * 3/1959
GB 896 914 C 5/1962

OTHER PUBLICATIONS

German Office Action dated Jun. 21, 2006.
English translation of German Office Action for DE 10 2005 048 394.1-12.

* cited by examiner

*Primary Examiner*—Thomas R Hannon
*Assistant Examiner*—James Pilkington
(74) *Attorney, Agent, or Firm*—Brinks, Hofer, Gilson & Lione

(57) ABSTRACT

A spindle drive and patient positioning system is provided. The spindle drive includes a drive that is operative to drive a spindle nut. An axially transportable spindle is circled by the spindle nut. A catch nut that is not in mutual engagement with the spindle has a predefined distance to the drive. When the spindle nut fails, the spindle is operative to move the catch nut into mutual engagement with the spindle. A switching element is fixed to the catch nut and includes an emergency off switch, which is activated by a switching sensor.

19 Claims, 5 Drawing Sheets

SPINDLE DRIVE AND A PATIENT POSITIONING SYSTEM

The present patent document claims the benefit of the filing date of DE 10 2005 048 394.1, filed Oct. 10, 2005.

BACKGROUND

1. Field

The present embodiments relate to a spindle drive and a patient positioning system.

2. Related Art

Spindle drives and threaded spindles are used in applications in which, for example, loads or system components have to be moved and precisely positioned. Spindle drives have been used in industrial applications such as machine tools and end user applications such as garage door openers. In addition, spindle drives are used in, for example, medical diagnostic and/or therapeutic devices (DT devices). For example, X-ray tube assemblies, X-ray image receivers, patient positioning systems, computer tomography equipment, magnetic resonance equipment or nuclear medicine and radiation therapy equipment, are moved and positioned using spindle drives.

Spindle drives may experience unidentified wear or mechanical failure, which creates considerable risks of injury and endangerment for the user or for other persons entering into contact with the spindle-driven apparatus, for example, in X-ray devices for the doctor or the patient. Generally, the spindle nut revolves on a threaded spindle, with an epicyclic gearing, for example, a recirculating ball gear. Unidentified wear, which leads to complete mechanical failure of the spindle drive, may be caused by the failure of the recirculating ball gear. If the balls of the recirculating ball gear are destroyed by wear, for example, then the recirculating ball gear is no longer in mutual engagement with the threaded spindle. The connection between the spindle and the mass to be moved is lost. The recirculating ball gear is no longer supported by the balls in the thread of the threaded spindle. The recirculating ball gear becomes freely movable. In a vertical spindle drive, the mass to be moved, in the worst scenario, falls down.

In order to reduce the risk of danger, due to an unforeseeable failure of the spindle drive, recirculating ball gears with catch nuts (safety nuts) are used. The catch nut is fixedly connected to the spindle nut and has a thread that is in mutual engagement with the thread of the threaded spindle, which is similar to the balls of the recirculating ball gear. The pitch of the thread of the catch nut here corresponds to the pitch of the thread of the spindle nut and to that of the thread of the threaded spindle. The catch nut can revolve jointly with the recirculating ball gear around the threaded spindle. For example, the thread of the catch nut revolves frictionlessly around the threaded spindle when the spindle nut, or, for example, the recirculating ball gear revolves truly around the spindle (i.e. within the predefined tolerances).

The catch nut is engaged when the spindle nut is no longer revolving truly around the spindle. For example, the spindle nut may be damaged or no longer revolve truly around the spindle because of excessive bearing play of the recirculating ball gear or destruction of the recirculating balls. When the spindle nut is damaged or no longer revolves truly around the spindle, the force closure between threaded spindle and recirculating ball gear is lost. Alternatively, the force closure between the catch nut and threaded spindle is established. An uncontrolled self-movement of the mass to be moved is then prohibited by the catch nut. The mass to be moved is prevented, for example, from falling down.

An operation of the spindle drive despite failure of the spindle nut is possible because the thread of the catch nut substantially corresponds to that of the spindle nut. When the spindle nut experiences mechanical failure, the catch nut steps in for the spindle nut and replaces it in its function.

Generally, a spindle drive and catch nut are not visible to a user, but are hidden, for example, behind panels or cladding parts. Accordingly, the failure of the spindle drive is not apparent to the user. If the spindle nut fails and the operation is continued on the basis of the catch nut, no further safeguard exists. If the catch nut subsequently fails, there complete failure of the spindle drive, for example, a height-adjusting device falls down.

Generally, in spindle drives with a fixed spindle nut and rotating spindle, the mutual connection of a catch nut and a spindle nut is frequently checked, for example, by an electrical device. For example, when the spindle nut fails and falls onto the catch nut, a mutual contact is formed, which is electrically or mechanically detectable. This mutual contact is detected and is used to activate an emergency off switch. However, in spindle drives with a fixed spindle, the spindle nut is driven and revolves around the spindle. Accordingly, checking the contact between the spindle nut and the catch nut is not readily possible because, for example, electrical contact between the two rotating nuts would be necessary. To create a contact between the two rotating parts is complicated. Standard contact types, for example, sliding contacts, are subject to wear and thus prone to error.

GB 896 914 C describes an apparatus for indicating an admissible wearing of a first nut. The first nut bears a load and, because of wearing, is subject to displacement along a threaded spindle. The apparatus contains a second nut, which bears no load and in which said threaded spindle engages. Only a relative axial displacement is allowed between the two nuts. The second nut has an adjustable stopper, which actuates a switch on the first nut whenever the relative axial distance between the two nuts falls below a value corresponding to the admissible wearing of the thread of the first nut. The switch is connected to a display means, which is switched on when the switch is actuated.

A spindle drive with a fixed spindle and revolving spindle nut and catch nut that is able to identify the failure of a spindle nut is desired.

SUMMARY

In one embodiment, a spindle drive includes a drive that is operative to drive a spindle nut. An axially transportable spindle is circled by the spindle nut. A catch nut that is not in mutual engagement with the spindle has a predefined distance to the drive. When the spindle nut fails, the spindle is operative to move the catch nut into mutual engagement with the spindle. A switching element is fixed to the catch nut and includes an emergency off switch, which is activated by a switching sensor. The switching element is operative to actuate the switching sensor when the catch nut is moved axially relative to the drive by axial movement of the spindle.

In one embodiment, a spindle drive has a drive, a spindle nut driven by the drive, a spindle circled by the spindle nut, and a catch nut that is constructed such that, while the spindle nut is intact, it is not in mutual engagement with the spindle and assumes a predefined distance to the drive. For example, if the spindle nut fails, the catch nut is brought, by axial movement of the spindle, into mutual engagement with the spindle. The spindle drive comprises a switching element, which is fixedly connected to the catch nut. The catch nut is moved axially within predefined motional limits. In another embodiment, an emergency off switch is activated by a switching sensor. The switching element actuates the switching sensor when the catch nut is moved axially relative to the drive by axial movement of the spindle.

In one exemplary embodiment, the mutual contact of the spindle nut and catch nut, for example, the two moving parts do not have to be checked. Alternatively, only the axial displacement of the catch nut relative to the drive, as a non-movable fixed part, is checked.

In another embodiment, the switching element is a switching tube that lies concentrically over the spindle nut. The switching element is rotation-invariant because of the tubular construction. In another embodiment, the spindle has additional cladding, which offers an optical protection and protection against unintended engagement in moving mechanical parts of the spindle drive.

In one embodiment, the spindle drive is vertically orientated in such a way that a height adjustment of the spindle is based on the revolution of the spindle nut. The spindle drive is used, for example, as the lifting device for a patient positioning system, for an X-ray stand or an equipment component such as a C-arm. The load to be lifted is heavy and may cause failure of the spindle nut. For example, when the spindle nut fails, the spindle nut and the heavy load falls down. In one embodiment, the catch nut is disposed above the spindle. The catch nut, in the event of failure of the spindle nut, falls down into mutual engagement with the spindle onto the spindle nut and is stopped by the spindle nut. Because of the spindle and load having fallen down, the switching element connected to the catch nut is simultaneously jointly moved, so that an instant and automatic actuation of the emergency off switch is guaranteed.

In another embodiment, the emergency off switch of the spindle drive is connected to a drive such that the drive is stopped and/or switched off by activation of the emergency off switch. The operation of the spindle drive, following failure of the spindle nut, for example, in a generally unsafe operating situation, is prohibited.

BRIEF DESCRIPTION OF THE DRAWINGS

Further advantageous embodiments emerge from the dependent patent claims and from the following figures and figure description, in which:

DETAILED DESCRIPTION

Figure 1:
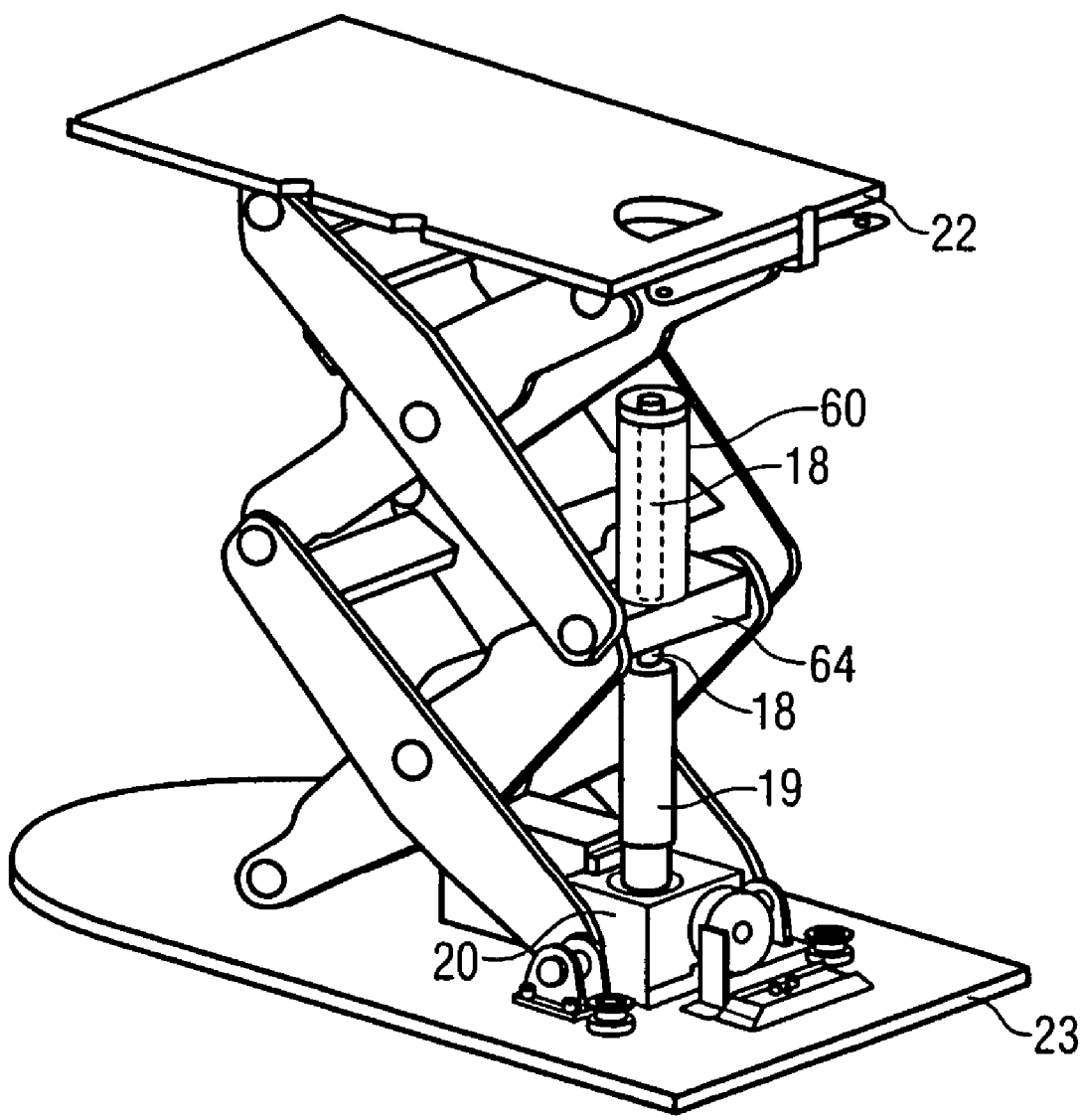
FIG. 1 illustrates a lifting unit with a spindle drive.

In FIG. 1, a lifting unit with a spindle drive is shown schematically. In one exemplary embodiment, the lifting unit is a component part of a patient positioning system and serves for adjusting the height thereof. In another exemplary embodiment, the lifting unit is a component part of a C-arm apparatus or of another DT device and serves for the height adjustment, for example, of a C-arm or of a radiation source.

In one embodiment, as shown in FIG. 1, the lifting unit includes a bottom base plate 23, on which both a double scissors and the spindle drive is mounted. A lifting plate 22 is linearly transported by the double scissors and the spindle drive relative to the base plate 23, for example, in the height direction. The spindle drive includes a drive 20, which drives the spindle nut 19. The spindle nut 19 revolves around the spindle 18, so that a recirculating ball spindle is formed. For example, the non-rotating spindle 18 is transported axially, for example, up or down, because of the revolution of the spindle nut 19 around the non-rotating spindle 18.

The top end of the spindle 18 runs in an immersion tube 60 (i.e. the top end intrudes into the immersion tube 60). The immersion tube 60 is connected to the spindle 18 and prevents the spindle 18 from being able to rotate. The immersion tube 60 is transported up or down by the movement of the spindle 18. The immersion tube 60 is fixedly connected to the cross bar 64 of the double scissors. For example, if the immersion tube 60 is transported up or down, then the cross bar 64 is respectively transported up or down. The cross bar 64 is a component part of the double scissors and is integrated in an axis of the scissors construction. The up or down movement of the cross bar 64 causes a shortening or lengthening of the double scissors and a height adjustment of the lifting plate 22.

In one embodiment, the inner diameter of the immersion tube 60 is wider than the outer diameter of the spindle nut 19. For example, upon lowering of the double scissors, the immersion tube 60 slides over the spindle nut 19 or the spindle nut 19 intrudes into the immersion tube 60. Accordingly, the lifting plate 22 is lowered as far as possible.

Figure 2:
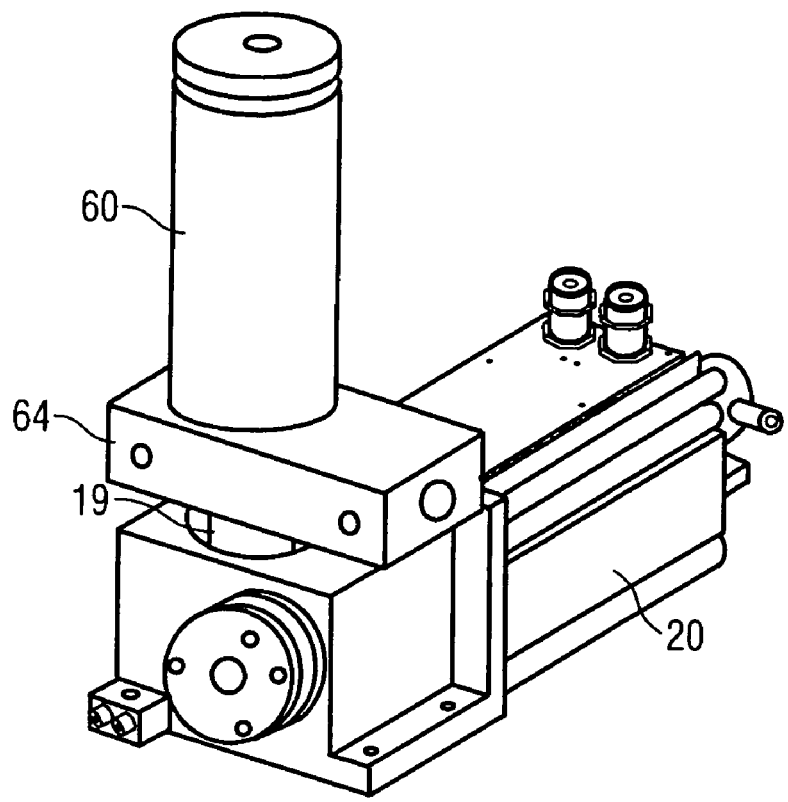
FIG. 2 illustrates a spindle drive with a component of the lifting unit.

In one embodiment, as shown in FIG. 2, the spindle drive is driven by a drive 20, which rotates the spindle nut 19. The spindle nut 19 revolves around the spindle (not shown), which is thereby moved up or down. The spindle is disposed or seated in the immersion tube 60 and is connected thereto in such a way that it is prevented from rotating. For example, the spindle is prevented from being transported along with the spindle nut 19. The immersion tube 60 is fixedly connected to the cross bar 64. In one embodiment, the cross bar 64 forms an axis of the double scissors of the lifting unit. The spindle drive adjusts the height of the double scissors construction via the cross bar 64.

Figure 3:
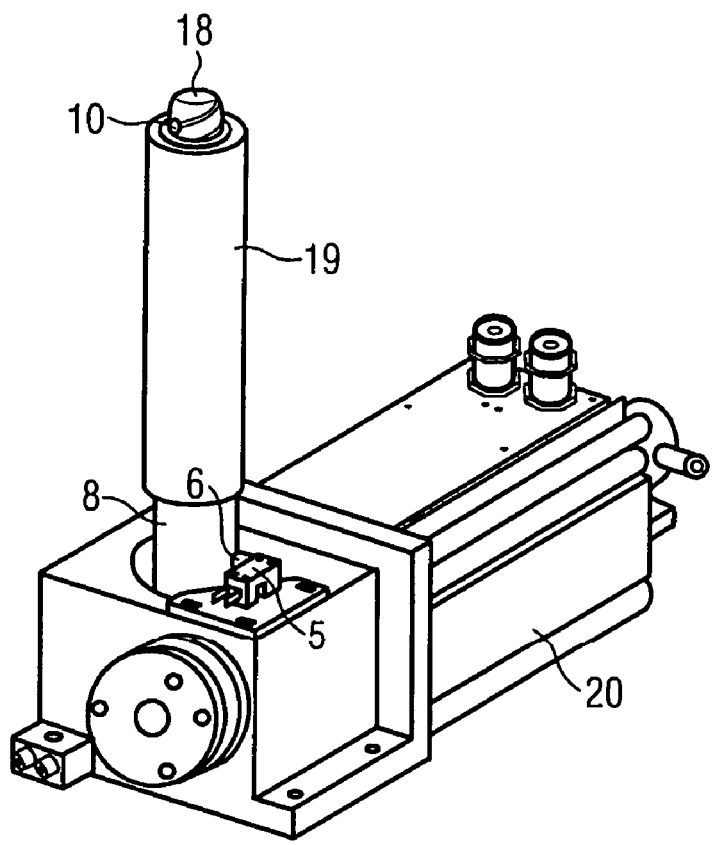
FIG. 3 illustrates a spindle drive with an emergency off switch.

In one embodiment, as shown in FIG. 3, the spindle drive includes a drive 20 that rotates the spindle nut 19, which revolves around the spindle 18. The spindle nut 19 is disposed on and fixedly connected to a spindle tube 8, which is driven by the drive 20. The catch nut 10 is disposed in the spindle nut 19 in such a way that, when the spindle nut 19 is rotated, the catch nut 10 is transported along with the spindle nut 19. In one embodiment, the spindle nut 19, as long as it is intact, is in mutual engagement with the spindle 18, for example, as a recirculating ball spindle via balls disposed in the thread. The catch nut 10 is normally not in mutual engagement with the spindle 18. In one embodiment, the spindle 18 and catch nut 10 do not contact each other. Accordingly, unintended wearing of the catch nut 10 is prevented. The catch nut 10, in contrast to the spindle nut 19, is therefore constructed as a standard screw nut without a friction-reducing ball recirculation.

In one embodiment, an emergency off switch 5 is fitted to the drive 20 or in the immediate vicinity of the spindle tube 8. The emergency off switch 5 has a push button 6, which is facing the spindle tube 8 but does not touch the spindle tube 8. The push button 6 is designed to be actuated by the switching tube (not represented in the figure) should the spindle nut 19 fail.

Figure 4:
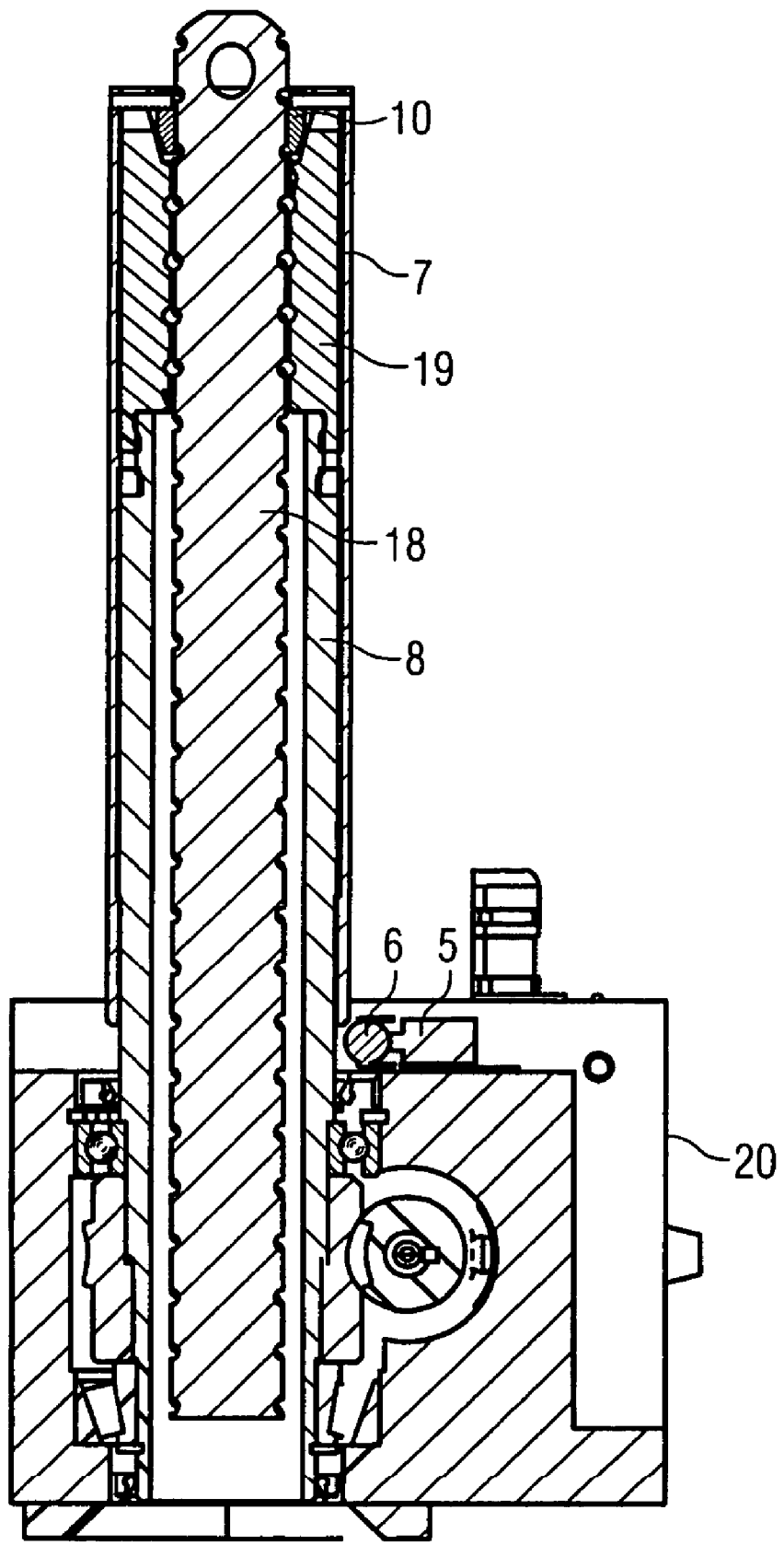
FIG. 4 illustrates a non-activated emergency off switch.

In one embodiment, as shown in FIG. 4, the drive 20 drives the spindle tube 8 via a worm gear (not shown). The spindle nut 19 is fixed to the spindle tube 8. The spindle nut 19 revolves using a ball recirculation around the spindle 18. The spindle 18 reaches through the spindle tube and the drive and is provided at the top end with a bolt eye. In a loaded state, for example, the top end of the spindle 18 bears the load to be raised or lowered. The spindle 18 is connected to the load (not shown) such that it is prevented from rotating. Depending on the construction, the bolt eye may be used to prevent the spindle 18 from rotating.

In one embodiment, as shown in FIG. 4, the catch nut 10 is disposed above the spindle nut 19. The catch nut 10 is connected to the spindle nut 19 such that, when the spindle nut 19 is rotated, the catch nut 10 is transported along with it. The catch nut 10 has an inner thread, which fits into the thread of the spindle 18. The catch nut 10 has no or only slight contact with the spindle 18, so that friction-induced wear is precluded. In one embodiment, it is not necessary for the catch nut 10 to have a friction-reducing ball recirculation. The catch nut 10 is disposed at a predefined distance to the spindle nut 19. It is fixedly connected to the switching tube 7. The switching tube 7 lies concentrically over the spindle nut 19 and the spindle tube 8. The switching tube 7 moves at least axially relative to the spindle nut 19 and the spindle tube 8, and not fixed to the spindle tube 8.

In one embodiment, an emergency off switch 5 with a push button 6 is disposed on the drive 20 and in the immediate vicinity of the spindle tube 8. The push button 6 is constructed as a ball.

In one embodiment, as shown in FIG. 4, the switching tube 7 does not actuate the push button 6, for example, the emergency off switch 5 is not activated. For example, the spindle nut 19 is intact and is working correctly.

Figure 5:
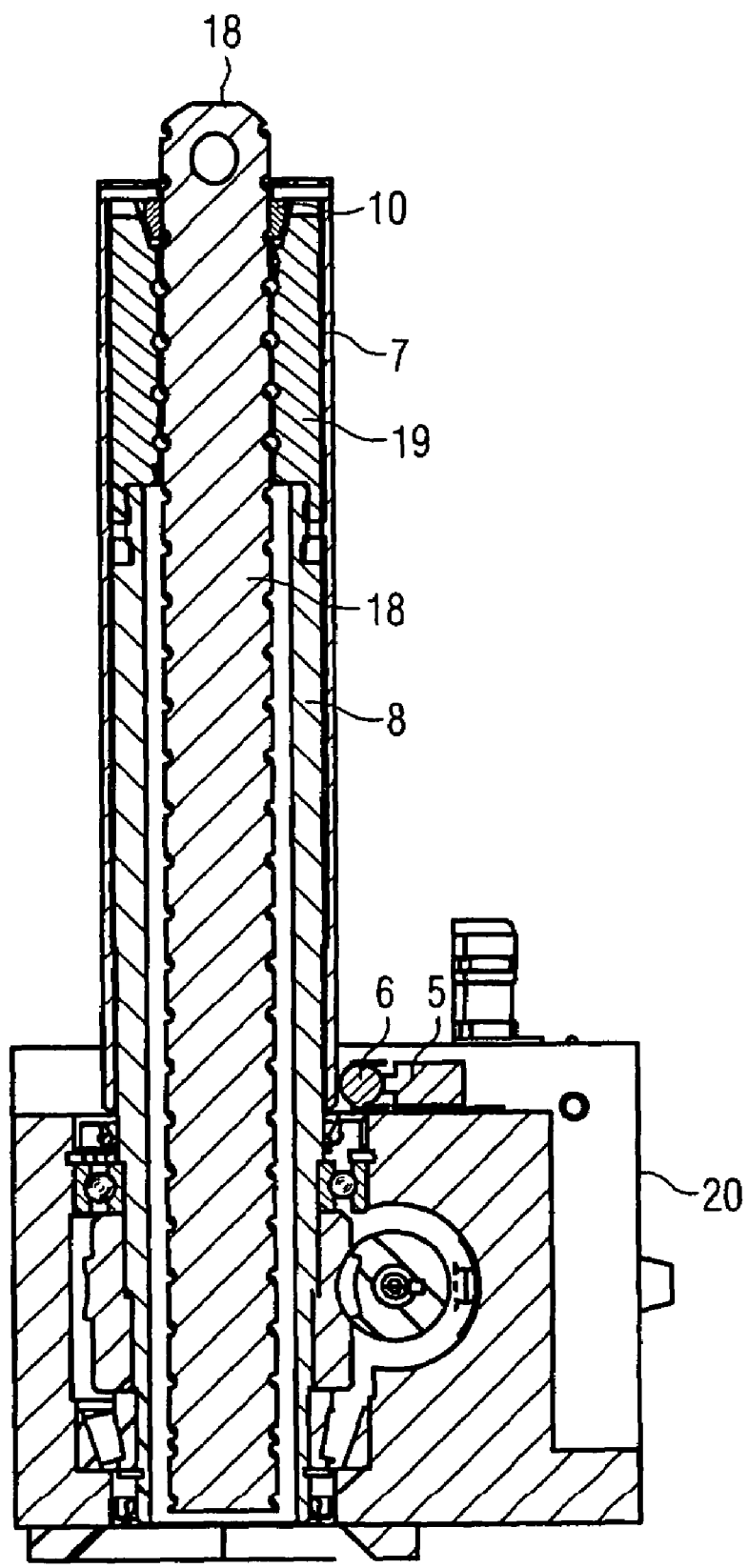
FIG. 5 illustrates an activated emergency off switch.

In FIG. 5, a spindle drive with a failed spindle nut 19 is described. The same reference symbols are used as in the preceding figure description.

In one embodiment, when the spindle nut 19 fails, the form closure to the spindle 18 is abolished because, for example, the balls of the ball recirculation of the spindle nut 19 have burst or the threads are worn. The spindle 18 is no longer held by the spindle nut 19, but falls down.

In one embodiment, when the spindle nut 19 fails, the catch nut 10 is operative. The thread of the spindle 18 enters into mutual engagement with the inner thread of the catch nut 10 because the spindle 18 has fallen down. The falling-down spindle is supported on the catch nut 10 by resting on the inner thread of the catch nut 10. When the spindle falls down, the catch nut 10 is transported along with it. The fall distance for the catch nut 10 is limited by the spindle nut 19, which remains fixed to the spindle tube 8. The spindle 18 and catch nut 10 fall down until the catch nut 10 hits the spindle nut 19. The fall distance is the distance between spindle nut 19 and catch nut 10 in the intact state.

In one embodiment, when the catch nut 10 falls down, the switching tube 7 connected thereto is transported along with it. The switching tube 7 falls just as far down as the catch nut 10. Consequently, the switching tube 7 enters into contact at the lower end with and actuates the push button 6. The push button 6 is pressed by the switching tube 7 to and actuates the emergency off switch 5.

In one embodiment, the emergency off switch 5 generates a signal that indicates the failure of the spindle nut 19. The signal is used to display an error report on a control unit, to prompt an automatic recording of the error report in a log file or to stop or switch off the drive 20 immediately. Immediate switching-off of the drive 20 ensures that the spindle drive, following failure of the spindle nut 19, cannot inadvertently continue to be operated, for example, because the failure has not been spotted by the operator.

Figure 6:
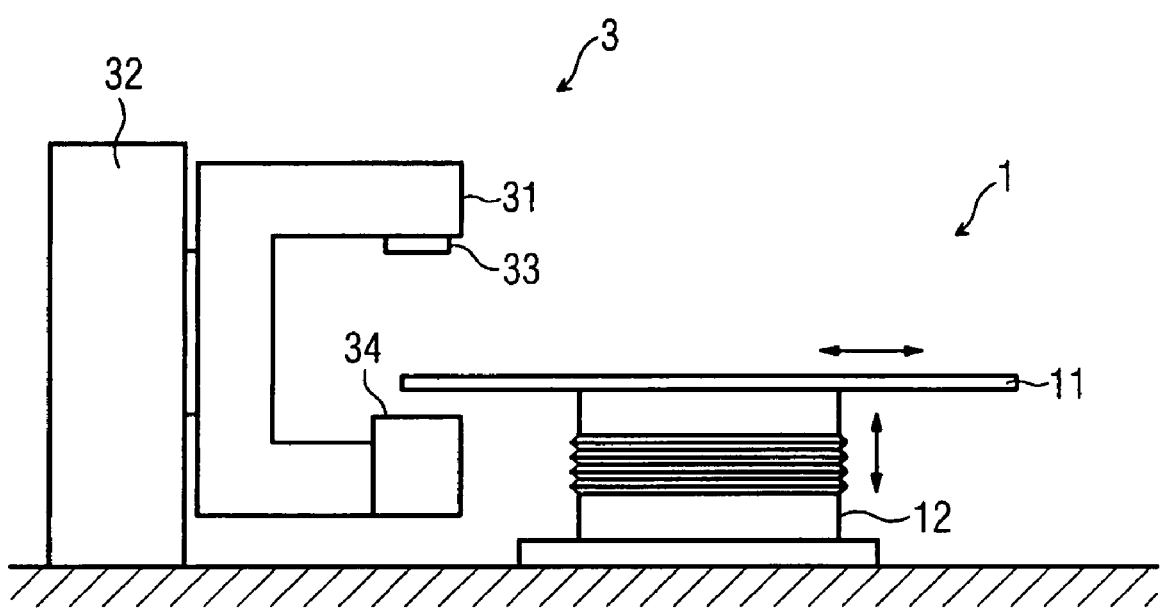
FIG. 6 illustrates a diagnostic and/or therapeutic apparatus.

In one embodiment, as shown in FIG. 6, a DT device 3 includes a C-arm 31, which has a beam source 33 and an image detector 34. The C-arm 31 is used, for example, to produce X-ray images, in the case of lower-energy X-ray radiation. In another embodiment, the C-arm 31 is used for therapeutic radiation, for example, in the case of higher-energy X-ray radiation. The C-arm 31 is mounted in a C-arm holder 32. The C-arm holder, for example, stands freely in the room or is embedded in a wall or ceiling of the room. In another embodiment, the C-arm 31 has the X-ray tube assembly 33 and the X-ray detector 34 positioned so a patient positioned using the patient positioning system 1 is scanned by the X-ray beam.

The patient positioning system 1 includes a support 11 onto which a patient is laid. The support 11 is displaced in the horizontal direction, which is indicated by a horizontally orientated double arrow. The support 11 is mounted in a floating arrangement on a base 12. The height of the support 11 is adjustable. The base 12 includes a lifting system (not represented in detail in the figure). The height adjustability is indicated by a vertically orientated double arrow.

The height adjustment of the support 11 is achieved by a lifting unit with a spindle drive. As described in connection with the preceding figures a height adjustment of the C-arm 31 is adjusted by such a spindle drive.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A spindle drive comprising:
    a drive operative to drive a spindle nut;
    an axially transportable spindle that is circled by the spindle nut;
    a catch nut that is not in contact with the spindle and has a predefined distance to the drive when the spindle nut is intact, wherein if the spindle nut fails, the catch nut is brought into contact with the spindle; and
    a switching element that is fixed to the catch nut and includes an emergency off switch, which is activated by a switching sensor, wherein the switching element is operative to actuate the switching sensor when the catch nut is moved axially relative to the drive by axial movement of the spindle,
    wherein the switching element includes a switching tube that circles the spindle nut.

2. The spindle drive as claimed in claim 1, wherein the spindle nut comprises a recirculating ball spindle.

3. The spindle drive as claimed in claim 1, wherein the switching sensor is a push button.

4. The spindle drive as claimed in claim 1, wherein the drive is disposed vertically and the spindle nut is operative to adjust the height of the spindle by revolution of the spindle nut, and
    wherein the catch nut is disposed above the spindle nut, the spindle is operative to fall down when the spindle nut fails, and the catch nut is operative to fall down in contact with the spindle onto the spindle nut and is stopped by the spindle nut when the spindle nut fails.

5. The spindle drive as claimed in claim 1, wherein the emergency off switch is connected to the drive and operative to stop the drive.

6. The spindle drive as claimed in claim 1, wherein the drive comprises a drive motor and a worm gear.

7. The spindle drive as claimed in claim 1, wherein the spindle nut is disposed on and fixedly connected to a spindle tube driven by the drive, and wherein the switching tube circles the spindle tube.

8. The spindle drive as claimed in claim 7, wherein the switching tube moves axially relative to the spindle nut and the spindle tube, and the switching tube is not fixed to the spindle tube.

9. A patient positioning system comprising:
a lifting unit; and
a spindle drive that includes:
a drive operative to drive a spindle nut;
an axially transportable spindle operative with the spindle nut;
a catch nut that is not in contact with the spindle and has a predefined distance to the drive, wherein if the spindle nut fails, the spindle is operative to move the catch nut into contact with the spindle;
and a switching element that is fixed to the catch nut and includes an emergency off switch, which is activated by a switching sensor, wherein the switching element is operative to actuate the switching sensor when the catch nut is moved axially relative to the drive by axial movement of the spindle,
wherein the switching element includes a switching tube that circles the spindle nut.

10. The patient positioning system as claimed in claim 9, wherein the spindle is fixed to a component of the lifting unit.

11. The patient positioning system as claimed in claim 10, wherein the spindle is operative to adjust the height of the lifting unit.

12. The patient positioning system as claimed in claim 9, wherein the spindle nut comprises a recirculating ball spindle.

13. The patient positioning system as claimed in claim 9, wherein the switching sensor is a push button.

14. The patient positioning system as claimed in claim 9, wherein the drive is disposed vertically and the spindle nut is operative to adjust the height of the spindle by revolution of the spindle nut, and
wherein the catch nut is disposed above the spindle nut, the spindle is operative to fall down when the spindle nut fails, and the catch nut is operative to fall down in contact with the spindle onto the spindle nut and is stopped by the spindle nut when the spindle nut fails.

15. The patient positioning system as claimed in claim 9, wherein the emergency off switch is connected to the drive and operative to stop the drive.

16. The patient positioning system as claimed in claim 9, wherein the drive comprises a drive motor and a worm gear.

17. The patient positioning system as claimed in claim 9, wherein the spindle drive is operative to adjust the height of the patient positioning system.

18. The patient positioning system as claimed in claim 9, wherein the spindle drive is operative to adjust the height of a therapeutic or diagnostic device.

19. The patient positioning system as claimed in claim 9, wherein the spindle drive is operative to adjust the height of a C-arm.

* * * * *